United States Patent [19]

Pfleger

[11] 4,221,218
[45] Sep. 9, 1980

[54] DISPOSABLE HYPODERMIC SYRINGE

[76] Inventor: Frederick W. Pfleger, 1152 Barbara Dr., Cherry Hill, N.J. 08003

[21] Appl. No.: 4,732

[22] Filed: Jan. 18, 1979

[51] Int. Cl.³ .............................................. A61M 5/00
[52] U.S. Cl. ......................... 128/218 D; 128/218 DA
[58] Field of Search ....... 128/218 R, 218 D, 218 DA, 128/218 P, 215, 216, 220, 234

[56] References Cited
U.S. PATENT DOCUMENTS

| 841,701 | 1/1907 | Delisle | 128/218 P |
|---|---|---|---|
| 3,811,441 | 5/1974 | Sarnoff | 128/218 DA |
| 3,930,499 | 1/1976 | Rimbaud | 128/218 DA |
| 4,011,868 | 3/1977 | Friend | 128/218 P |
| 4,084,588 | 4/1978 | Koenig | 128/218 R |

Primary Examiner—John D. Yasko

[57] ABSTRACT

A hypodermic syringe with a fluid chamber comprising a straight piece of glass or inert material tubing not attacked by the fluid held, rubber sealing pieces for sealing each end of the straight tube and a surrounding casing used to secure the rubber seals and provide the means to mount a needle fluid ejection rod and means for activating the unit to form a hypodermic syringe used for injection of medicines, liquids, etc.

9 Claims, 2 Drawing Figures

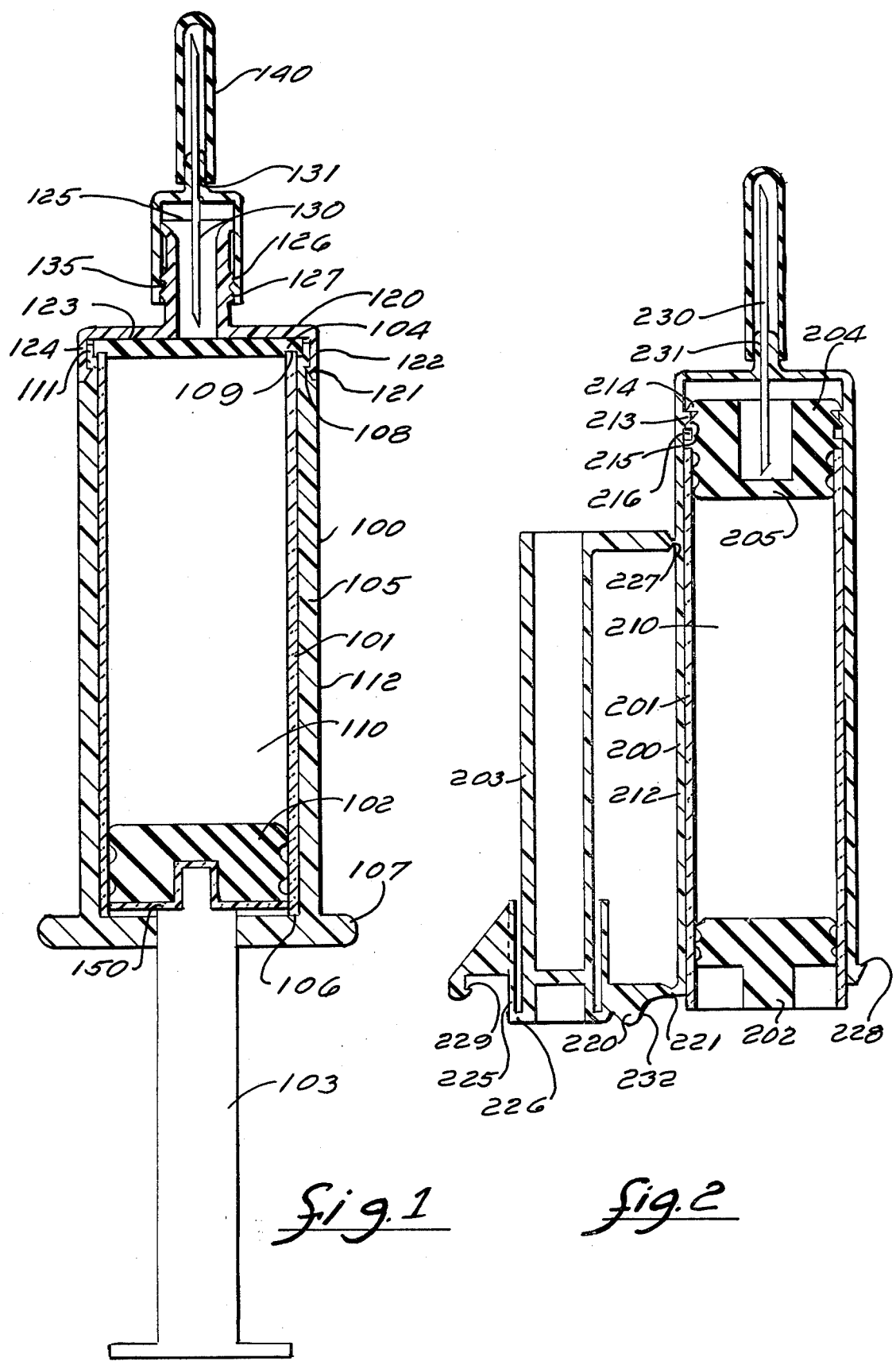

DISPOSABLE HYPODERMIC SYRINGE

BACKGROUND OF THE INVENTION

In the field of hypodermic syringes the original syringes were made from glass formed into a liquid holding cartridge with the needle attached. These syringes were provided with a fluid ejecting rod which was withdrawn from the bottom surface to fill the syringe or moved toward the bottom for ejecting the fluid. This filling and emptying of the syringe being performed by the user. In sterile applications disposable syringes of similar configurations were developed so that after use the syringes were discarded. A further development in the syringe field was to have the disposable syringes prefilled. These syringes consisted of the same elements as the syringes described above but in many cases made of plastic to reduce cost. The fluids were packaged under sterile packaging conditions in factories and/or drug laboratories. Since many fluids that are used in hypodermic syringes attack many materials including plastics, further developments were made to the prefilled disposable syringe which required the fluid chamber to be made from inert material such as glass. In order to use glass in this application contouring of the glass at both ends became a necessity. Since contouring of glass to close tolerances is a very expensive operation and since close tolerances are a requirement in high production filling operations, the use of contoured glass is a limiting factor in the ability to meet present and projected production requirements. As a result, it is highly desirable to eliminate the contouring of the glass and instead use a straight glass tube, since this the least expensive form for this glass item. It is also desirable to have the glass tube cut by standard production techniques rather than having to lap or grind each end of the glass to exacting requirements. The other components of the syringe can be manufactured from low cost materials and processes such as plastics and metal stamping since these components do not come in contact with the fluids used in the syringe. The front and rear seal of the syringe can still be made of rubber as is standard in existing prefilled syringes.

Since the use of prefilled disposable syringes is growing rapidly, it is important that the cost of the syringe is as low as possible, that the reliability of the syringe is as high as possible, and that the components used to make up the overall syringe are capable of being handled on high speed production equipment. It is also important that the syringe be tamper proof and easily activated. Since certain uses of syringes requires large volume of fluid, many of the existing prefilled syringes are getting large and cumbersome to handle and store as well as being difficult to activate. As a result, storage and shipping form factors of the syringe becomes important due to existing storage area confines. Syringes in use today do not meet all of these requirements.

SUMMARY OF THE INVENTION

It is therefore an object of this invention to provide a hypodermic syringe in which the fluid holder is a straight tubular part made of inert material.

It is a further object of this invention to provide a hypodermic syringe in which it does not require expensive special finishing techniques to finish the ends of the straight tubular part.

It is a further object of this invention to provide a hypodermic syringe which utilizes plastics and/or production metal techniques to form inexpensive chamber closing elements for sealing the fluid in the glass tubular part.

It is a further object of this invention to provide a hypodermic syringe in which the plastic and/or metal closing elements are provided with means to make the completed enclosure tamper proof, that is, making it impossible for a person to remove the fluid contents from the chamber without destroying the package integrity.

It is a further object of this invention to provide a hypodermic syringe in which a straight glass tube is used and the needle element is packaged so that only in time of use will the needle come in contact with the fluid.

It is a further object of this invention to provide a hypodermic syringe in which the low cost enclosure members provide a complete fluid chamber and only at time of use is a needle attached to the unit and activated. This is done after removing a sterile sealing element. It is a further object of this invention to provide a hypodermic syringe that is easy to activate for use.

It is a further object of this invention to provide a hypodermic syringe which is packaged in such a manner that the storage configuration of the unit lends itself to ease of handling and convenience in storing.

Other objects of the invention will become apparent from the following specifications and drawings which form part of this disclosure.

This invention therefore consists of unique features of construction, materials and combinations which will provide a construction of minimum cost and high reliability, the scope of which will be indicated by the appended claims.

BRIEF DESCRIPTION OF DRAWINGS

FIG. 1 is a longitudinal sectional view through the length of a syringe showing the configuration of a straight glass fluid container mounted into a structure in which the syringe is activated by moving the needle holder into the stationary fluid container.

FIG. 2 is a longitudinal sectional view of a syringe with a straight glass fluid container in which the syringe is activated by movement of the glass fluid container into the stationary needle so that the needle enters the fluid container.

DESCRIPTION OF PREFERRED EMBODIMENT

Referring to FIG. 1, the disposable syringe 100 comprises a straight glass tubing 101 forming the cylinder of a fluid container 110. In one end of the glass fluid container 110 is a rubber fluid ejecting piston 102 of such configuration that the fluid in the fluid container will not leak past the rubber seal. Secured to the rubber fluid ejecting piston 102 is a plunger rod 103 which in this particular embodiment is shown fastened permanently to the rubber fluid ejecting piston 102. As is well known in the art, when the syringe is in storage or deactivated condition the plunger rod 103 could act as a needle cover or stored over a separate needle cover. It stored in this manner the plunger rod 103 would be removed from its storage position over the needle and snap-filled or threaded into the rubber fluid ejecting piston 102 during the fluid ejection when the syringe is activated. In order to seal the other end of the fluid container 110, a rubber disc 104 is fitted over the opposite end of the straight glass tubing 101. This rubber disc 104 could also be a rubber plug which could fit into the inside of the straight glass tubing 101 similar to the plug shown in FIG. 2. The straight glass tubing 101 is mounted in a plastic sleeve 105 such that one end of the straight glass tubing 101 rests against an inner surface 106 formed at the one end of the plastic sleeve 105. The plastic sleeve 105 is also formed at this end into an extended flange 107 which is used as a finger retainer during fluid injection. The other end of the plastic sleeve 105 is designed to cooperate with a cap member 120 which together with rubber disc 104 is used to secure and seal the straight glass tubing 101. The cap member 120 is provided with a locking tab 121 extending inwardly from a ring 122. Locking tab 121 acts with locking groove 108 of plastic sleeve 105 in such a manner that the clearance between the glass end 109 of the straight glass tubing 101 and the inner surface 123 of cap member 120 is of such a dimension that it provides compression of the rubber disc 104 between the glass end 109 and the inner surface 123. This compression of the rubber disc 104 then acts to seal the fluid container 110 and locate the straight glass tubing 101 in the plastic sleeve 105. A flange 111 of the plastic sleeve 105 extends beyond the end of the plastic sleeve in such a manner as to cradle and locate the rubber disc 104 while the cap member 120 is being assembled. As a result, it can be seen that an adequate seal of the fluid container 110 can be obtained by controlling the length of the straight glass tubing 101, the thickness of the rubber disc 104 and the relationship of the inner surface 123 to the inner surface 106. The external surface 112 of the plastic sleeve 105 and the external surface 124 of the cap member 120 are designed to be in line so that it is virtually impossible to disassemble the cap member 120 from the plastic sleeve 105 after locking tab 121 is locked into position locking groove 108.

Before being able to eject fluid from the fluid container of the needle which transfers the fluid from the container into the patient to be injected must penetrate the rubber disc 104. In this particular disclosure this is accomplished by use of a double-ended needle 130 which is securely mounted to a hub 131. Although there are many methods known for a double-ended needle to puncture a rubber sealing element, in this particular embodiment I have shown the commonly known snap cover system. In this system the cap member 120 is provided with an annular ring 125 which acts as an internal guide for hub 131. An annular inner locking flange 135 of hub 131 locates between two locking rings 126 and 127 of cap member 120 when the hub 131 is assembled to cap member 120 for normal storage. The hub therefore is retained in such a manner that the needle is adjacent to the rubber disc 104, but will not penetrate the disc. In order to activate the syringe, hub 131 is pushed inwardly towards the syringe in such a manner that the annular inner locking flange 135 snaps over locking ring 127. In this movement annular inner locking flange 135 of hub 131 moves into locking engagement with locking ring 127 of the cap member 120. When hub 131 is moved into active position and annular inner locking flange 135 and locking ring 127 are engaged, it is impossible to move hub 131 back into inactive position without distruction, since the shape of locking ring 127 and annular inner locking flange 135 are formed such that they produce a permanent lock. In the motion of hub 131 onto cap member 120 one end of the double-ended needle penetrates the rubber disc 104. In order to use this syringe with the straight glass tubing 101, it is now only necessary to remove a needle cap 140, insert the other end of the double-ended needle 130 into the patient and expel the fluid from the fluid container 110 by pushing the rubber fluid ejecting piston 102 inwardly by means of plunger rod 103.

In order to consider a syringe of this type tamper proof it should be impossible to extract the fluid from the fluid container without activating the syringe and preventing it from being reset into inactivated position without destroying or modifying any of the parts. In this manner a user can see if the syringe was previously activated or if any of the parts were modified. As was previously described in reference to FIG. 1, once the syringe is activated it cannot be reset. Since the seal between the straight glass tubing 101 and the rubber fluid ejecting piston 102 lies behind the inner surface 106 of plastic sleeve 105, it is not possible to penetrate this seal to extract the fluid. The only possible place therefore to extract the contents of the syringe would be by inserting a hollow needle through the rubber which lies behind the plunger rod 103, if the plunger rod was not present. In order to prevent this, a shield 150 is assembled to the rubber fluid ejecting piston 102 and in activation the plunger rod is inserted into shield 150. The shield 150 is of such a configuration that it also lies behind inner surface 106 so that it is impossible to remove the shield without destroying other parts. As a result, the syringe shown in FIG. 1 is practically tamper proof.

The configuration shown in FIG. 1, namely, the storage of the plunger rod assembled to the fluid ejecting piston, assembled to the needle cover or assembled to the needle hub acting as a cover, is suitable for relatively small dosage syringes. If the fluid to be injected is of large volume, the assembly shown in FIG. 1 becomes very long due to the length requirements of the fluid storage chamber, thus making the syringe pack a very unwieldly unit. In some cases where larger injections are made, the assembly configuration as shown in FIG. 1 can lead to a syringe package with an overall length of 12" or longer. As a result, the syringe shown in FIG. 2 is a straight glass tube syringe in which the plunger rod is assembled parallel and adjacent to the body of the syringe.

As shown in FIG. 2, the syringe 200 comprises a fluid container 210 formed by a straight glass tubing 210. One end of the straight glass tubing 201 is sealed with a rubber fluid ejecting piston 202. The straight glass tubing 201 is secured in a plastic casing 212 and is held in a storage or deactivated position by means of locating flange 213 mounted to the inside surface of the plastic casing 212. Locating flange 213 lies between retaining rings 214 and 215 on a rubber plug 204. As a result, in storage or deactivated position the straight glass tubing 201 is held in position by the interlocking action of locating flange 213 and retaining rings 214 and 215. In this position a double-ended needle 230, securely mounted to a boss 231, is in close proximity to penetrating membrane 205 of rubber plug 204. In order to activate the syringe it is necessary to move the straight glass tubing 201 with rubber fluid ejecting piston 202 and rubber plug 204 inwardly so that the double-ended needle 230 penetrates the penetrating membrane 205 of rubber plug 204. When the straight glass tubing and the rubber plug 204 are thus moved, locating flange 213 moves from locating between locating rings 214 and 215 to locating into the void 216 of rubber plug 204 beyond locating ring 215. Locating flange 213 and locating rings 214 and 215, as shown, are of such a configuration that they prevent moving back to previous position. Therefore, it is not possible to return the fluid container to inactivated condition.

In order to move the straight glass tubing 201 inwardly into plastic casing 212, the casing is provided at its outer end with a pivoting member 220 pivotal at a flexing hinge 221 between the pivoting member 220 and plastic casing 212. Pivoting member 220 comprises the flexing hinge 221, a guide member 225, a plunger rod 203 and a latch member 229. Plunger rod 203, the guide member 225 and the latch member 229, together with mating latch member 228, are all effectively one piece.

When the syringe is to be converted from inactivated condition to active condition the membrane section 227 is broken, thus the plunger rod 203 is free from plastic casing 212 and free to rotate counterclockwise, FIG. 2, on flexing hinge 221. In the rotation of the guide member 225 at flexing hinge 221 a caming surface 232 on guide member 225 engages the outer end of the straight glass tubing 201. This caming surface 232 during the rotational movement cams the straight glass tubing 201 inwardly, thus moving the rubber plug 204 and the straight glass tubing 201 into active condition as previously described. After the plunger rod 203 and guide member 225 are rotated approximately 180°, the latch member 229 engages the mating latch member 228 to hold the plunger rod in alignment with the axis of the syringe. In this position the plunger rod, breakable membrane section 226 are broken and the plunger rod 203 can be engaged with the rubber fluid ejecting piston 202. Since the needle has pierced the penetrating membrane 205 pressure on the plunger rod 203 and rubber fluid ejecting piston 202 forces the liquid from the syringe. In order to make the syringe, as shown in FIG. 2, tamper proof a breakable sealing member 240 is applied to the outer edge of the straight glass tubing 201. The plunger rod 203 being capable of breaking this seal when changing the syringe from inactivated condition to active condition.

As a result of the above description when read in light of the accompanying drawing, it has been shown that a straight glass tubing can be used in a disposable hypodermic syringe which is activated by either the movement of the needle or the movement of the fluid container. The syringe still has all of the desired properties of disposable syringes plus having the added desired properties of being tamper proof and more compact. Although the above description and drawings show a preferred embodiment of the invention, this invention should not be limited to this description, but should be controlled by the following claims.

What is claimed is:

1. A disposable hypodermic syringe comprising a straight glass tubing having a distal end and a proximal end, said distal end and said proximal end having an opening equal to the internal dimension of said tubing, a slideable plunger in said proximal end, a compressible seal for sealing said distal end, a casing for said tubing having a locating surface for locating said proximal end of said tubing, a closing member for closing said tubing in said casing, connecting means comprising separate cooperating mating elements one of which is located on said closing member and one of which is located on said casing such that in the connected position said connecting means cooperate to retain said closing member to said casing, a cannula having an inner end and an outer end mounted to said closing member in a non-activated position with said inner end adjacent to said compressible seal and pierceable through said seal in an activated position and a plunger rod adaptable to said slideable plunger.

2. In a disposable hypodermic syringe according to claim 1 including a solid disc mounted in said slidable plunger and said plunger rod adaptable to said solid disc.

3. In a disposable hypodermic syringe according to claim 1 wherein said compressible seal extends beyond the outer surface of said tubing.

4. In a disposable hypodermic syringe according to claim 1 wherein said locating surface extends inwardly a distance substantially past the inner surface of said tubing.

5. In a disposable hypodermic syringe comprising a straight glass tubing having a distal end and a proximal end, said distal end and said proximal end having an opening equal to the internal dimension of said tubing, a slidable plunger in said proximal end, a compressible seal held in compressed condition by the inside surface of said glass tubing in said distal end, a pair of locating groves related to said compressed seal, a casing for said tubing, locating means in said casing for locating said glass tubing and said compressible seal in said casing by engagement with said locating groves, a double ended cannular mounted in said casing such that one end of said cannular lies in pre-piercing position with said seal when said seal is located in one of said pair of groves and in pierced engagement with said seal when said seal is located in the other of said pair of groves, a pivotal guide pivotable from a position parallel to the axis of said casing to a position in line with the axis of said casing, a plunger rod slidably mounted in said pivotal guide, said pivotal guide engageable with said proximal end in pivoting from said parallel to said in line position to move said tubing and said compressible seal from one of said locating groves to the other of said locating groves.

6. In a disposable hypodermic syringe according to claim 5 wherein said plunger rod is aligned with said moveable plunger where said pivotal guide is in said in line position with axis.

7. In a disposable hypodermic syringe according to claim 5 including attaching means for attaching said plunger rod to said casing when said plunger rod is in said parallel to the axis position.

8. In a disposable hypodermic syringe according to claim 5 including latching means to latch said pivotal member in said in line position with axis.

9. A disposable hypodermic syringe according to claim 1 wherein said cooperating mating elements include an annular grove as one of said elements and a latching member as the other of said mating elements.

* * * * *